United States Patent [19]
Sawyer et al.

[11] Patent Number: 5,498,540
[45] Date of Patent: Mar. 12, 1996

[54] METHOD FOR CULTURING INSECT CELLS IN A MEDIUM CONTAINING FISH SERUM

[75] Inventors: Evelyn S. Sawyer; Philip J. Sawyer, both of Kennebunkport, Me.

[73] Assignee: Sea Run Holdings, Inc., Kennebunkport, Me.

[21] Appl. No.: 362,236

[22] Filed: Dec. 22, 1994

Related U.S. Application Data

[63] Continuation-in-part of Ser. No. 200,639, Feb. 23, 1994, Pat. No. 5,401,653.
[51] Int. Cl.$^6$ .............................. C12N 5/00; A61K 35/56; A61K 35/60
[52] U.S. Cl. ................... 435/240.2; 435/240.21; 435/240.1; 424/531
[58] Field of Search ................. 424/531; 435/240.1, 435/240.2, 240.21

[56] References Cited

U.S. PATENT DOCUMENTS

| | | | |
|---|---|---|---|
| T102,602 | 1/1983 | Isom et al. | 119/4 |
| 4,449,480 | 5/1984 | Isom et al. | 119/4 |
| 4,454,227 | 6/1984 | Roder | 435/240 |
| 5,024,947 | 6/1991 | Inlow et al. | 435/240.31 |

OTHER PUBLICATIONS

ATCC Catalogue of Cell Lines & Hybridomas, 6th Ed., 1988, pp. 342–355.
Jokoby et al., "Methods in Ezymology", vol. LVIII, 1979, Academic–Press Inc., pp. 44–93, see entire document.
In Vitro Cellular & Development Biology, vol. 25, No. 9, Sep. 1989, Chou. et al., "Isolation of Melanized Cell Lines with Stable Phenotypes From a Goldfish Erythrophoroma Cell Line and Cryopreservation of These Cells by the Use of Autologous Serum", pp. 813–820, see entire document.
Parasitol Res., vol. 77, No. 8, 1991, Hamers et al, "In Vitro Study of the Impact of Fish Sera on the Survival and Fine Structure of the Eel-Pathogenic Acanthocephalan Paratenuisentis Ambiguus", pp. 703–708, see entire document.
Cell Differentiation and Development, vol. 28, No. 2, Nov. 1989, Chou et al., "Reversible Dedifferentiation and Redifferentiation of a Melanized Cell Line from a Goldfish Tumor", pp. 105–117, see entire document.
"Manufacturers Warned Not to Use Bovine Origin Materials From BSE Countries" FDA Veterinarian, Mar./Apr. 1994.

*Primary Examiner*—Marian C. Knode
*Assistant Examiner*—Jean C. Witz
*Attorney, Agent, or Firm*—Thomas M. Champagne; Jon L. Roberts; Roberts & Associates

[57] ABSTRACT

A method for culturing insect cells using fish serum. The method uses serum extracted from the blood of fish to culture insect cells for various purposes. The technique has the key advantages of consistent quality, low cross reactivity, safety from infectious agents that would endanger researchers or humans and animals receiving cell culture products as therapy and has appropriate nutrients to maintain the growth of insect cells. Fish serum is used together with designated defined medium to allow insect cells to grow and populations to be maintained. The method may also be used with lumpfish to prevent the attachment of insect cells to cultureware. Serum is derived from the blood of captive stocks of fishes raised under control conditions.

14 Claims, No Drawings

METHOD FOR CULTURING INSECT CELLS IN A MEDIUM CONTAINING FISH SERUM

This is a continuation-in-part of U.S. patent application Ser. No. 08/200,639, filed Feb. 23, 1994, now U.S. Pat. No. 5,401,653.

FIELD OF THE INVENTION

The present invention relates generally to the culture of cells and more specifically to the culture of insect cells using a serum derived from fish. The technique has significant advantages over the more commonly used technique of using blood serum derived from fetal calves or other mammals as more fully set forth below.

BACKGROUND OF THE INVENTION

Animal cell culture is a basic technique in the fields of biology and medicine. The production of living cells in vitro, that is, in the laboratory, permits numerous applications that would be difficult or impossible in vivo, that is, in the living animal. The culture of animal cells requires a defined medium containing specific quantities of certain chemicals, and in addition for most cells, up to 15% of an undefined nutrient medium, usually fetal bovine serum (FBS). Serum from newborn calves and other mammals is also used, but FBS is preferred because of its high level of growth factors and low cross-reactivity with other animal cells.

The production of FBS in this country is an estimated 700,000 liters annually, worth $300 to $400 million. The industry obtains fetal calves for bleeding from slaughter houses, or in some cases, rears herds of cattle for this purpose. These herds are held in as isolated a situation as possible in order to prevent disease. Whole blood is obtained aseptically (by syringe) from an animal, the blood is centrifuged to separate cells from serum, and the serum is filtered to 0.22 microns to remove most infections agents. Often, serum is heated to 56° C. to inactivate the complement system, a group of immune proteins.

Insect cell culture has also been conducted for many years to develop control methods for this important animal group, and has been used as a model for biological processes in humans and higher animals. More recently, insect cell culture and a virus vector have become valuable tools for the expression of foreign genes. This technique is superior to the production of foreign proteins by bacteria as higher yields, better "copies", and more complex eukaryotic proteins can be obtained (Smith et al., 1983). Some examples of the recombinant proteins produced by insect cell expression systems are human interferon and interleukin-2, substances that are injected as therapy in human subjects.

An example of the current method of protein production includes the following steps: 1) culture of an insect cell line (*Spodoptera frugiperda*); 2) insertion of the desired foreign gene in the baculovirus, Autographa Californica Polyhedral Virus (Ac NPV); 3) infection of the insect cell line with this virus; and 4) extraction of the resulting foreign protein from the infected insect cells.

Contamination of cell cultures because of infectious organisms in serum can be a serious problem. Bacteria, fungi, viruses, and mycoplasma have been isolated from bovine serum. A decade ago, mycoplasma from bovine serum was the second major group of contaminants found in cell culture (Barile, 1977). Now, animal sera are routinely screened for mycoplasma, viruses, and other known contaminants. However, a more serious cause for concern is an all-protein infectious agent called a prion for which no test is available (Prusiner, 1982). This prion causes a fatal brain disease in mammals called Bovine Spongiform Encephalopathy (BSE) or "mad cow disease". BSE occurs in sheep, cows, and other mammals, and is most likely the cause of similar neuro-degenerative diseases such as such as Creutzfeld-Jakob disease in humans. In Britain since 1986, BSE resulted in the destruction of over 100,000 cattle and fears for contamination of the meat supply or other animal products. The disease has also turned up in cattle in many other countries. Consequently, serum from these countries cannot be imported for use in the U.S.

During insect cell culture procedures, most insect cells are maintained in a defined medium plus 10% FBS. Therefore, any infectious agent in the FBS could contaminate a recombinant protein made by the cells, and could be transmitted to humans receiving this protein as therapy.

The method of the present invention is especially timely as BSE has recently been found in Canadian cattle (Campbell, 1993) and is strongly implicated as the cause of death in Wisconsin mink which were fed protein meal made from dairy cow carcasses (Marsh, 1993). In Europe there is evidence of the disease in humans receiving contaminated human growth hormone (Knauer, 1993).

SUMMARY OF THE INVENTION

It is therefore an object of the present invention to provide a method of extracting a serum from fish that allows the culture of insect cells.

It is yet another objective of the present invention to provide a serum that does not provide any danger from BSE or other pathogens to researchers or to humans and animals receiving medicinal products from insect cell culture.

It is a further object of the present invention to use a serum for cell culture that is free from various mammalian infectious agents that can invalidate the results of scientific testing relating to the culture of insect cells.

It is a further objective of the present invention to create a serum supply of consistent quality for use in cell culture.

It is still a further objective of the present invention to provide a means to enhance the supply of blood serum that is available for research or production in the biotechnology field specifically for the culture of insect cells.

These and other objects and advantages of the present invention will be apparent to those of ordinary skill in the art after examination of the description and appended claims.

The present invention is a method of using fish serum instead of bovine or other mammalian sera for insect cell culture. Fish serum offers advantages of safety from mammalian infectious agents and can be used for cell culture applications that now employ bovine or other mammalian sera, and for applications where these sera are ineffective or unsafe.

The ideal serum for insect cell culture would provide the nutrients and growth factors that maintain insect cells and support their growth. In addition, the serum should 1) be consistent in quality; 2) have serum immune proteins unlike those of insects for low cross-reactivity; 3) be free of infectious agents that would contaminate cell lines or cell culture products, or endanger researchers or humans and animals receiving products made by cell culture; and 4) provide the nutrients and growth factors that maintain insect cells and support their growth.

Sera from several species of aquacultured fishes can be used to grow insect cells. Research was conducted with four species of aquacultured fish, representing three families of teleosts; two salmonids, the rainbow trout and its seawater form the steelhead (*Oncorhynchus mykiss*); the Atlantic Salmon (*Salmo salar*); one cyclopterid, the lumpfish (*Cyclopterus lumpus*); and one ictalurid, the channel catfish (*Ictalurus punctatus*). Serum from these fishes is effective for insect cell culture and meets the characteristics of the ideal serum including consistency, low cross-reactivity, safety, and control of content.

Until the past few years, serum from fish would have been inconsistent in quality, because wild stocks (even within the same species) vary in diet, habitat, genetics, life history, and reproductive status. This inconsistency would influence the reproducibility of cell culture experiments, and make fish serum unsuitable for cell culture research. Now, by using domesticated stocks reared in aquaculture facilities, fish serum can be obtained with product consistency similar to serum from herds of cattle reared for this purpose. The essential requirement is for donor fish to be reared under consistent and therefore reproducible conditions, not necessarily the nature or specifics of these conditions. The reproducibility of conditions reduces variability in serum content, and yields lot-to-lot consistency of serum—an important factor in cell culture research.

As previously stated, a major advantage of fish serum for insect cell culture is safety. Serum from fishes is unlikely to contain infectious agents harmful to mammals including humans. Fish are cold-blooded animals with body temperatures that approximate the waters where they live. Therefore their pathogens, especially those of cold-water fishes, prefer temperatures well below the body temperatures of most mammals.

Fish serum is unlikely to cause unwanted cross-reactions with insect cells. Fish are an evolutionary distinct group of vertebrates remote from the insects.

Sera from fishes produced through aquaculture offer additional advantages such as control of environment, genetics, and nutrition of donor animals.

Levels of certain substances in fish blood can be controlled by procedures that would be impossible with mammals for biological or regulatory reasons. For example, mammalian genetic triploids are not viable, but in salmonids, triploids live and grow normally and serum from the female triploid contains no sex steroids (Schreck and Moyle, 1990). Conversely, the sexual maturity of donor fish can be induced by light or hormone injections if high sex steroid serum is desired. Also, fish can be held under conditions unacceptable for mammals, such as total darkness, to increase certain hormones such as melatonin in serum.

DETAILED DESCRIPTION OF THE PRESENT INVENTION

Using the present invention, the culture of two commonly used lines of insect cells in fish serum has been demonstrated. The fish serum used was taken from two species of salmonids, the rainbow trout and the steelhead (*Oncorhynchus mykiss*), and the Atlantic salmon (*Salmo salar*), the lumpfish (*Cyclopterus lumpus*), and the channel catfish (*Ictalurus punctatus*). These species were used because consistent and reproducible methods for their production are well established, large numbers of these species are reared in commercial aquaculture and therefore large amounts of serum can be obtained, and individual fish are large enough so that blood can be drawn easily. Other species of aquacultured fish fit these criteria, especially the sturgeon and the striped bass.

The process begins with the consistent and reproducible conditions under which donor fish are reared. All fish used as serum sources are 1) progeny of domesticated broodstock, 2) inspected for disease according to the American Fisheries Society Blue Book standards, 3) sexually immature, 4) in the log-phase of growth, 5) larger than two pounds, 6) reared by standard husbandry methods appropriate to the species as described in Piper (1988), and 7) fed commercially manufactured pelleted feed of a composition consistent with that recommended by Halver (1972) and commonly used for each species. Rainbow trout are reared in freshwater; steelhead, salmon, and lumpfish are reared in seawater.

Water temperature at the time of bleeding is 8° C. to 12° C. The fish are starved for five days before bleeding to reduce serum levels of proteolytic enzymes, lipids, and non-protein nitrogen (NPN). Each fish is stunned by a blow to the fish's head, by immersion in ice-water, or by immersion in water containing $CO_2$ or other fish anesthetic, the objective being to stun the fish to a level of loss of reflex reactivity (unconsciousness) as defined by Schreck and Moyle (1990). Whole blood is then drawn by syringe from the dorsal aorta, or in the case of the lumpfish, the caudal vein. Blood is allowed to clot for up to 2 hours, and is then centrifuged at 1100 × g for at least 10 minutes. Serum is removed from the collection tubes, sterilized by passing through a 0.22μ filter, and frozen at −70° C. No heat treatment is used or needed.

Spodoptera cells are used as one example of an insect cell line. They are grown in flasks or other vessels in Grace's medium supplemented with TC Yeastolate and Lactalbumin Hydrolysate and 10% FBS at 27° C. in a closed atmosphere.

Cells growing in 10% FBS must be adapted first to lower levels of FBS before they can be cultured in similar low levels of fish serum.

When the cells in the flasks have reached the log phase of growth, the process of weaning to lower FBS levels begins. The medium plus 10% FBS is removed by aspiration or pipette from each flask, and replaced with medium plus 7.5% FBS. These flasks are placed in an incubator and the cells are allowed to grow and increase in number for 48 hours. At this time the medium with 7.5% FBS is removed from the flasks and replaced with medium plus 5% FBS. The process may be repeated to lower FBS levels to 2.5% or 1%. The weaning process takes up to 10 days to acclimate cells to the lower concentrations of FBS.

Cells growing in the flasks containing medium plus 5% or 2.5% or 1% FBS are then harvested using standard trypsinization techniques, washed with serum-free medium, centrifuged at 300 g for 3.5 minutes at room temperature, counted in a hemocytometer, and resuspended in new 25 $cm^2$ tissue culture flasks containing serum-free medium. Aliquots from these flasks containing $5 \times 10^4$ cells/ml (by calculation) are then seeded in new flasks containing 5 ml of medium plus thawed fish serum as described above, at a concentration of 2.5% or 5% (v/v). Flasks containing the cells and media are then incubated at 37° C. in 5% $CO_2$/95% air.

At these concentrations of fish serum, cells will grow normally, the same as would be expected if they were cultured in FBS. When the cells are stained with a hematoxylin stain for observation, those cultured with 1% or 2.5% fish serum are normal and qualitatively similar to those cultured in media containing FBS. Cells cultured at 5% fish serum appear normal except for small lipid-filled vacuoles in the cytoplasm.

At this stage, insect cells can be subcultured for experimental or commercial purposes using fish serum as a replacement for FBS, in either flasks or suspension culture.

The method was repeated for Drosophila sp cells using Schneider's Insect Medium and 2.5% fish serum.

Results show that insect cells survive and grow in sera from all species of fishes tested. Insect cells in lumpfish serum survived and did not attach for 48 hours but attached normally when FBS was then added. Compared to the FBS control, insect cells grown in fish serum showed no obvious difference in appearance, and for lumpfish and steelhead serum, cell growth was similar to growth in FBS. Compared to cells in FBS, final cell numbers were lower and attachment less for cells grown in sera from the other fish species tested.

DISCUSSION

The effectiveness of fish serum for growth of insect cells is almost certainly influenced by lipid content, sexual maturity of the donor fish (as reflected in serum steroids), and the growth rate of donor fish.

Serum lipid in the fish species tested was high. Typical triglycerides were greater than 400 mg/dL and cholesterol was greater than 450 mg/dL, ten times or more higher than those of FBS. High serum lipoproteins are potentially growth inhibitory (Ito et al., 1982), therefore it is inferred that for some insect species lower lipid content in fish serum would improve cell growth.

The best performing sera were from fishes in their maximum growth phase, and beginning (3–4 months before) sexual maturity.

Although only two insect cell line were tested with sera from several species of aquacultured fish, similar results can be expected with other closely related lepidopteran cell lines such as *Mamestra brassicae* or Bombyx sp. (Davis et al., 1993). In addition to Drosophila and Spodoptera, other important insect cell lines and sera from other species of fish may be substituted for those disclosed here.

Preferred and alternate methods of the present invention for culturing insect cells using fish serum have now been described in detail It is to be noted, however, that this description of these particular embodiments is merely illustrative of the principles underlying the inventive concept. Other species of fish and other insect cell lines may be substituted for those disclosed herein. It is therefore contemplated that various modifications of the disclosed embodiments will, without departing from the spirit and scope of the invention, be apparent to persons skilled in the art.

REFERENCES

Anonymous, 1994. "Manufacturers warned not to use bovine-origin materials from BSE countries". *FDA Veterinarian*, March/April 1994, page 8.

Barile, M. F. 1977. "Mycoplasma Contamination of Cell Cultures —a Status Report". *Cell Culture and its Applications* (R. T. Acton and J. D. Lynn, Eds.) pages 291–334.

Barnes, R. D. 1963. *Invertebrate Zoology*. W. B. Saunders Co. Philadelphia, Penna. pages 297–298.

Freshney, R. I. 1987. *Animal Cell Culture—A Manual of Basic Techniques*. J. Wiley & Sons, N.Y.

Halver, J. E. 1972 *Fish Nutrition*. Academic Press, New York.

Kingman, S. 1993. "London Meeting Explores the Ins and Outs of Prions". *Science* 262: 180–181.

Pennak, R. W. 1953. *Freshwater Invertebrates of the United States*.

Piper, R. G. 1983. *Fish Hatchery Management*. U.S. Department of the Interior, Fish and Wildlife Service. Washington, D.C.

Pollard, J. W. and Walker, J. M. 1990. "Basic Cell Culture". *Methods in Molecular Biology*, Volume 5; Animal Cell Culture. Humana Press, Clifton, N.J. pages 1–12.

Schreck, C. B. and Moyle, P. B., 1990. *Methods in Fish Biology*, pp. 223–232. American Fisheries Society, Bethesda, Md.

Wolf, K. 1988. *Fish Viruses and Fish Viral Disease*, p. 108. Cornell University Press, Ithaca, N.Y.

We claim:

1. A method of culturing insect cells comprising:
   a. seeding live insect cells in a vessel containing a defined culture medium plus 10% fetal bovine serum;
   b. incubating the cells and medium;
   c. allowing the cells to grow and increase in numbers;
   d. subculturing the cells;
   e. removing the defined culture medium and fetal bovine serum from the vessel and adding defined culture medium with a lower concentration of fetal bovine serum;
   f. harvesting the cells;
   g. washing the cells with the defined culture medium;
   h. centrifuging the cells at 300 g for about 3.5 minutes at room temperature;
   i. resuspending the cells in a second vessel containing defined culture medium;
   j. seeding at least a portion of the cells in a third vessel containing defined culture medium and fish serum in a concentration of about 2.5% to about 5%; and
   k. incubating the cells and medium.

2. The method of claim 1, wherein the fish serum is prepared by:
   a. raising fish under controlled conditions such that the diet, habitat, genetics, life history, and reproductive status of the fish remains substantially constant and reproducible;
   b. starving the fish for up to about forty-eight hours;
   c. stunning the fish by non-toxic methods until the fish is unconscious;
   d. withdrawing whole blood from the fish;
   e. allowing the blood to clot;
   f. centrifuging the blood until the blood serum is separated from the blood cells;
   g. removing the serum; and
   h. sterilizing the serum.

3. The method of claim 1, wherein removing the defined culture medium and fetal bovine serum from the vessel and adding defined culture medium with a lower concentration of fetal bovine serum includes:
   a. removing the defined culture medium and fetal bovine serum from the vessel and adding defined culture medium with 7.5% fetal bovine serum;
   b. incubating the cells and medium;
   c. allowing the cells to grow and increase in numbers;
   d. subculturing the cells; and
   e. removing the defined culture medium and fetal bovine serum from the vessel and adding defined culture medium with 5% fetal bovine serum.

4. The method of claim 1, wherein removing the defined culture medium and fetal bovine serum from the vessel and adding defined culture medium with a lower concentration of fetal bovine serum includes:

a. removing the defined culture medium and fetal bovine serum from the vessel and adding defined culture medium with 7.5% fetal bovine serum;
b. incubating the cells and medium;
c. allowing the cells to grow and increase in numbers;
d. subculturing the cells;
e. removing the defined culture medium and fetal bovine serum from the vessel and adding defined culture medium with 5% fetal bovine serum;
f. incubating the cells and medium;
g. allowing the cells to grow and increase in numbers;
h. subculturing the cells; and
i. removing the defined culture medium and fetal bovine serum from the vessel and adding defined culture medium with 2.5% fetal bovine serum.

5. The method of claim 1, wherein removing the defined culture medium and fetal bovine serum from the vessel and adding defined culture medium with a lower concentration of fetal bovine serum includes:

a. removing the defined culture medium and fetal bovine serum from the vessel and adding defined culture medium with 7.5% fetal bovine serum;
b. incubating the cells and medium;
c. allowing the cells to grow and increase in numbers;
d. subculturing the cells;
e. removing the defined culture medium and fetal bovine serum from the vessel and adding defined culture medium with 5% fetal bovine serum;
f. incubating the cells and medium;
g. allowing the cells to grow and increase in numbers;
h. subculturing the cells;
i. removing the defined culture medium and fetal bovine serum from the vessel and adding defined culture medium with 2.5% fetal bovine serum;
j. incubating the cells and medium;
k. allowing the cells to grow and increase in numbers;
l. subculturing the cells; and
m. removing the defined culture medium and fetal bovine serum from the vessel and adding defined culture medium with 1% fetal bovine serum.

6. The method of claim 1, wherein the insect cells are Spodoptera cells.

7. The method of claim 1, wherein the insect cells are Drosophila cells.

8. A method of culturing insect cells comprising:

a. seeding live insect cells in a vessel containing a defined culture medium plus 10% fetal bovine serum;
b. incubating the cells and medium;
c. allowing the cells to grow and increase in numbers;
d. subculturing the cells;
e. removing the defined culture medium and fetal bovine serum from the vessel and adding defined culture medium with a lower concentration of fetal bovine serum;
f. harvesting the cells;
g. washing the cells with the defined culture medium;
h. centrifuging the cells at 300 g for about 3.5 minutes at room temperature;
i. resuspending the cells in a second vessel containing defined culture medium;
j. seeding the cells in a third vessel containing defined culture medium and thawed fish serum in a concentration of about 2.5% to about 5%; and
k. incubating the cells and medium.

9. The method of claim 8, wherein the fish serum is prepared by:

a. raising fish under controlled conditions such that the diet, habitat, genetics, life history, and reproductive status of the fish remains substantially constant and reproducible;
b. starving the fish for up to about forty-eight hours;
c. stunning the fish by non-toxic methods until the fish is unconscious;
d. withdrawing whole blood from the fish;
e. allowing the blood to clot;
f. centrifuging the blood until the blood serum is separated from the blood cells;
g. removing the serum;
h. sterilizing the serum; and
i. freezing the fish serum.

10. The method of claim 8, wherein removing the defined culture medium and fetal bovine serum from the vessel and adding defined culture medium with a lower concentration of fetal bovine serum includes:

a. removing the defined culture medium and fetal bovine serum from the vessel and adding defined culture medium with 7.5% fetal bovine serum;
b. incubating the cells and medium;
c. allowing the cells to grow and increase in numbers;
d. subculturing the cells; and
e. removing the defined culture medium and fetal bovine serum from the vessel and adding defined culture medium with 5% fetal bovine serum.

11. The method of claim 8, wherein removing the defined culture medium and fetal bovine serum from the vessel and adding defined culture medium with a lower concentration of fetal bovine serum includes:

a. removing the defined culture medium and fetal bovine serum from the vessel and adding defined culture medium with 7.5% fetal bovine serum;
b. incubating the cells and medium;
c. allowing the cells to grow and increase in numbers;
d. subculturing the cells;
e. removing the defined culture medium and fetal bovine serum from the vessel and adding defined culture medium with 5% fetal bovine serum;
f. incubating the cells and medium;
g. allowing the cells to grow and increase in numbers;
h. subculturing the cells; and
i. removing the defined culture medium and fetal bovine serum from the vessel and adding defined culture medium with 2.5% fetal bovine serum.

12. The method of claim 8, wherein removing the defined culture medium and fetal bovine serum from the vessel and adding defined culture medium with a lower concentration of fetal bovine serum includes:

a. removing the defined culture medium and fetal bovine serum from the vessel and adding defined culture medium with 7.5% fetal bovine serum;
b. incubating the cells and medium;

c. allowing the cells to grow and increase in numbers;
d. subculturing the cells;
e. removing the defined culture medium and fetal bovine serum from the vessel and adding defined culture medium with 5% fetal bovine serum;
f. incubating the cells and medium;
g. allowing the cells to grow and increase in numbers;
h. subculturing the cells;
i. removing the defined culture medium and fetal bovine serum from the vessel and adding defined culture medium with 2.5% fetal bovine serum;
j. incubating the cells and medium;
k. allowing the cells to grow and increase in numbers;
l. subculturing the cells; and
m. removing the defined culture medium and fetal bovine serum from the vessel and adding defined culture medium with 1% fetal bovine serum.

13. The method of claim 8, wherein the insect cells are Spodoptera cells.

14. The method of claim 8, wherein the insect cells are Drosophila cells.

* * * * *